US012645723B1

(12) United States Patent
    Rajmohan et al.

(10) Patent No.: US 12,645,723 B1
(45) Date of Patent: Jun. 2, 2026

(54) AUTOMATED PROMPT OPTIMIZATION FOR GENERATIVE LANGUAGE MODELS

(71) Applicant: Microsoft Technology Licensing, LLC, Redmond, WA (US)

(72) Inventors: Saravanakumar Rajmohan, Redmond, WA (US); Drishti Goel, Bengaluru (IN); Akshay Uttama Nambi, Bengaluru (IN); Xuchao Zhang, Sammamish, WA (US); Chetan Bansal, Seattle, WA (US); Supriyo Ghosh, Bangalore (IN); Prathamesh Subodh Deshpande, Bangalore (IN); Raghav Magazine, Bengaluru (IN)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 19/072,695

(22) Filed: Mar. 6, 2025

(51) Int. Cl.
    *G06F 16/334* (2025.01)
    *G06F 11/3604* (2025.01)
    *G06F 16/332* (2019.01)
    *G16H 50/20* (2018.01)
    *G16H 50/70* (2018.01)

(52) U.S. Cl.
    CPC ...... *G06F 16/3347* (2019.01); *G06F 11/3604* (2013.01); *G06F 16/3322* (2019.01); *G16H 50/20* (2018.01); *G16H 50/70* (2018.01)

(58) Field of Classification Search
    None
    See application file for complete search history.

(56) References Cited

U.S. PATENT DOCUMENTS

| | | | | |
|---|---|---|---|---|
| 2020/0105413 A1* | 4/2020 | Vladimirova | .......... | G16H 20/30 |
| 2022/0301713 A1* | 9/2022 | Amatya | ................ | G16B 20/40 |
| 2025/0355905 A1* | 11/2025 | Brenner | ................ | G06F 16/338 |

OTHER PUBLICATIONS

Abdin, et al., "Phi-3 Technical Report: A Highly Capable Language Model Locally on Your Phone", Retrieved from: In Repository of arXiv:2404.14219v1, Apr. 22, 2024, 12 Pages.
(Continued)

*Primary Examiner* — Thu N Nguyen
(74) *Attorney, Agent, or Firm* — Schwegman Lundberg & Woessner, P.A.

(57) ABSTRACT

Techniques for generating optimized input prompts for generative language models combines automated prompt refinement with intelligent context retrieval. A prompt optimization service automatically refines initial prompt instructions through controlled mutation and evaluation cycles using multiple generative language models. A context management service maintains a vector database of historical examples pre-encoded as embedding vectors, enabling efficient retrieval of semantically similar examples for new tasks. A dynamic prompt generator assembles optimized prompts by combining refined instructions with relevant historical examples and task context. The system supports deployment with both large language models and smaller fine-tuned models, enabling efficient operation across diverse applications. Configurable parameters allow balancing optimization quality against computational costs. The system maintains efficiency through single-call mutations, fast vector similarity search, and support for compact fine-tuned models that reduce resource requirements while preserving response quality.

20 Claims, 5 Drawing Sheets

200

(56) References Cited

OTHER PUBLICATIONS

Agarwal, et al., "PromptWizard: Task-Aware Prompt Optimization Framework", In Repository of arXiv:2405.18369v2, Oct. 3, 2024, 33 Pages.

Ahmed, et al., "Recommending Root-cause and Mitigation Steps for Cloud Incidents Using Large Language Models.", In Repository of arXiv:2301.03797v2, Feb. 9, 2023, 13 Pages.

Azad, et al., "Picking Pearl from Seabed: Extracting Artefacts from Noisy Issue Triaging Collaborative Conversations for Hybrid Cloud Services", In Proceedings of Thirty-Sixth AAAI Conference on Artificial Intelligence, vol. 36, No. 11, Jun. 28, 2022, pp. 12440-12446.

Bansal, et al., "DeCaf: Diagnosing and Triaging Performance Issues in Large-Scale Cloud Services", In Proceedings of 42nd International Conference on Software Engineering: Software Engineering in Practice, May 23, 2020, pp. 201-210.

Chen et al., "Evaluating Large Language Models Trained on Code," In Repository of arXiv:2107.03374v2, Jul. 14, 2021, 35 pages.

Chen, et al., "An Empirical Investigation of Incident Triage for Online Service Systems", In 2019 IEEE/ACM 41st International Conference on Software Engineering: Software Engineering in Practice (ICSE-SEIP). IEEE, 2019, 10 Pages.

Chen, et al., "Continuous Incident Triage for Large-Scale Online Service Systems", In 2019 34th IEEE/ACM International Conference on Automated Software Engineering (ASE). IEEE, 2019, pp. 364-375.

Chen, et al., "InstructZero: Efficient Instruction Optimization for Black-Box Large Language Models", In Repository of arXiv:2306.03082v1, Jun. 5, 2023, 15 Pages.

Chen, et al., Automatic Root Cause Analysis via Large Language Models for Cloud Incidents, Proceedings of the Nineteenth European Conference on Computer Systems, Apr. 22, 2024, pp. 674-688.

Fernando, et al., "Promptbreeder: Self-Referential Self-Improvement via Prompt Evolution", In Repository of arXiv:2309.16797v1, Sep. 28, 2023, 64 Pages.

Ganatra, et al., "Detection Is Better Than Cure: A Cloud Incidents Perspective", In Proceedings of the 31st ACM Joint European Software Engineering Conference and Symposium on the Foundations of Software Engineering, Nov. 30, 2023, pp. 1891-1902.

Gao, et al., "An Empirical Study on Crash Recovery Bugs in Large-Scale Distributed Systems", In Proceedings of the 2018 26th ACM joint meeting on european software engineering conference and symposium on the foundations of software engineering, Oct. 26, 2018, 12 Pages.

Ghosh, et al., "How to Fight Production Incidents? An Empirical Study on a Large-Scale Cloud Service", In Proceedings of the 13th Symposium on Cloud Computing, Nov. 7, 2022, pp. 126-141.

Goel, et al., "eARCO: Efficient Automated Root Cause Analysis with Prompt Optimization", In Repository of arXiv:2504.11505v1, Apr. 15, 2025, 11 Pages.

Goel, et al., "X-Lifecycle Learning for Cloud Incident Management using LLMs", In Companion Proceedings of the 32nd ACM International Conference on the Foundations of Software Engineering, Jul. 10, 2024, pp. 417-428.

Guo, et al., "Connecting Large Language Models with Evolutionary Algorithms Yields Powerful Prompt Optimizers", In Repository of arXiv:2309.08532v1, Sep. 15, 2023, 18 Pages.

Jain, et al., "Jigsaw: Large Language Models meet Program Synthesis", In Repository of arXiv:2112.02969v1, Dec. 6, 2021, 12 Pages.

Jiang, et al., "How to Mitigate the Incident? An Effective Troubleshooting Guide Recommendation Technique for Online Service Systems", In Proceedings of the 28th ACM Joint Meeting on European Software Engineering Conference and Symposium on the Foundations of Software Engineering, Nov. 8, 2020, pp. 1410-1420.

Jiang, et al., "Xpert: Empowering Incident Management with Query Recommendations via Large Language Models", In Repository of arXiv:2312.11988v1, Dec. 19, 2023, 13 Pages.

Jimenez, et al., "SWE-bench: Can Language Models Resolve Real-World GitHub Issues?", In Repository of arXiv:2310.06770v1, Oct. 10, 2023, 46 Pages.

Johnson, et al., "Billion-Scale Similarity Search with GPUs", In Repository of arXiv:1702.08734v1, Feb. 28, 2017, 12 Pages.

Joshi, et al., "Repair Is Nearly Generation: Multilingual Program Repair with LLMs", Proceedings of the AAAI Conference on Artificial Intelligence. vol. 37. No. 4, 2023, pp. 5131-5140.

Karpukhin, et al., "Dense Passage Retrieval for Open-Domain Question Answering", In Proceedings of the Conference on Empirical Methods in Natural Language Processing, Nov. 16, 2020, pp. 6769-6781.

Levi, et al., "Intent-based Prompt Calibration: Enhancing prompt optimization with synthetic boundary cases", In Repository of arXiv:2402.03099v1, Feb. 5, 2024, 17 Pages.

Li, et al., "AUGER: Automatically Generating Review Comments withPre-training Models", Proceedings of the 30th ACM Joint European Software Engineering Conference and Symposium on the Foundations of Software Engineering, Nov. 9, 2022, pp. 1009-1021.

Li, et al., "Automating Code Review Activities by Large-Scale Pre-training", In Repository of arXiv:2203.09095v2, Oct. 11, 2022, 13 Pages.

Lin, et al., "Use Your INSTINCT: INSTruction optimization using Neural bandits Coupled with Transformers", In Forty-first International Conference on Machine Learning, 2024, 31 Pages.

Liu, et al., "What bugs cause production cloud incidents?", Proceedings of the Workshop on Hot Topics in Operating Systems, May 13, 2019, pp. 155-162.

Srinivas, et al., "Intelligent Monitoring Framework for Cloud Services: A Data-Driven Approach", In Proceedings of the 46th International Conference on Software Engineering: Software Engineering in Practice, 2024, pp. 381-391.

Wadhwa, et al., "CORE: Resolving Code Quality Issues using LLMs", Proceedings of the ACM on Software Engineering, vol. 01, No. FSE, Jul. 12, 2024, pp. 789-811.

Xu, et al., "A Systematic Evaluation of Large Language Models of Code", Proceedings of the 6th ACM SIGPLAN international symposium on machine programming, Jun. 13, 2022, pp. 1-10.

Zhang, et al., "Automated Root Causing of Cloud Incidents using In-Context Learning with GPT-4", Companion Proceedings of the 32nd ACM International Conference on the Foundations of Software Engineering., Jul. 10, 2024, pp. 266-277.

Zhang, et al., "Understanding and Detecting Software Upgrade Failures in Distributed Systems", Proceedings of the ACM SIGOPS 28th Symposium on Operating Systems Principles, Oct. 26, 2021, pp. 116-131.

Zhou, al., "Large Language Models Are Human-Level Prompt Engineers", In Repository of arXiv:2211.01910v1, Nov. 3, 2022, 40 pages.

* cited by examiner

AUTOMATED PROMPT OPTIMIZATION FOR GENERATIVE LANGUAGE MODELS

TECHNICAL FIELD

The present disclosure relates generally to automated prompt optimization techniques for generative language models, including small language models (SLMs) and large language models (LLMs), and more particularly to systems and methods for dynamically generating and refining input prompts through iterative mutation and synthesis processes. Specifically, the disclosure describes approaches for using generative language models to automatically optimize prompts through a multi-stage refinement process that includes mutation, scoring, critique and synthesis steps to improve model outputs across various applications. The technical field encompasses artificial intelligence (AI), machine learning, and specifically the development of prompt optimization systems that can efficiently generate high-quality prompts while addressing challenges in computational efficiency, prompt quality, and model performance. The technical field further includes techniques for combining optimized prompts with dynamically selected examples and contextual information, for in-context learning, to enhance AI model responses.

BACKGROUND

Artificial intelligence (AI)-based systems that utilize generative language models have become increasingly integral across various domains, including natural language processing, automated content creation, data analysis, and user interaction interfaces. Generative language models are designed to process textual input and produce coherent, contextually relevant output, making them capable of generating responses, summarizing text, translating languages, answering questions, and more.

The core functionality of these systems is predicated on the receipt of an input prompt. A prompt is a textual input provided to the system, typically comprising one or more sentences or structured text designed to elicit a specific type of output from the generative language model. The generative language model processes the input prompt using its trained parameters, which are derived from extensive pre-training on large-scale text corpora, to generate the corresponding output. The quality, relevance, and usefulness of the output largely depend on the content and structure of the input prompt.

Prompts act as the interface through which users interact with generative language models. They encapsulate the user's intent and serve as the foundation for the system's interpretation of the task at hand. A well-crafted prompt effectively communicates the user's intent, provides necessary context, and reduces ambiguity, thereby enabling the model to produce an output aligned with the user's expectations. Conversely, poorly formulated prompts can lead to suboptimal, irrelevant, or even erroneous outputs, undermining the utility of the system.

Given the diversity of applications and the complexity of tasks performed by generative language models, ensuring that a prompt is appropriately crafted is essential for maximizing the effectiveness of these AI-based systems. While some users may possess the expertise required to compose clear and effective prompts, many applications necessitate automated or semi-automated approaches to optimize prompts for improved performance and user satisfaction.

The increasing reliance on generative language models in critical and high-value applications further underscores the importance of prompt quality. As these systems are deployed in environments ranging from customer support to content creation and decision-making, the ability to generate accurate and contextually appropriate responses becomes paramount. As a result, the formulation and optimization of input prompts have emerged as key areas of interest and development within the field of AI.

BRIEF DESCRIPTION OF THE DRAWINGS

Embodiments of the present invention are illustrated by way of example and not limitation in the figures of the accompanying drawings, in which.

DETAILED DESCRIPTION

Figure 1:
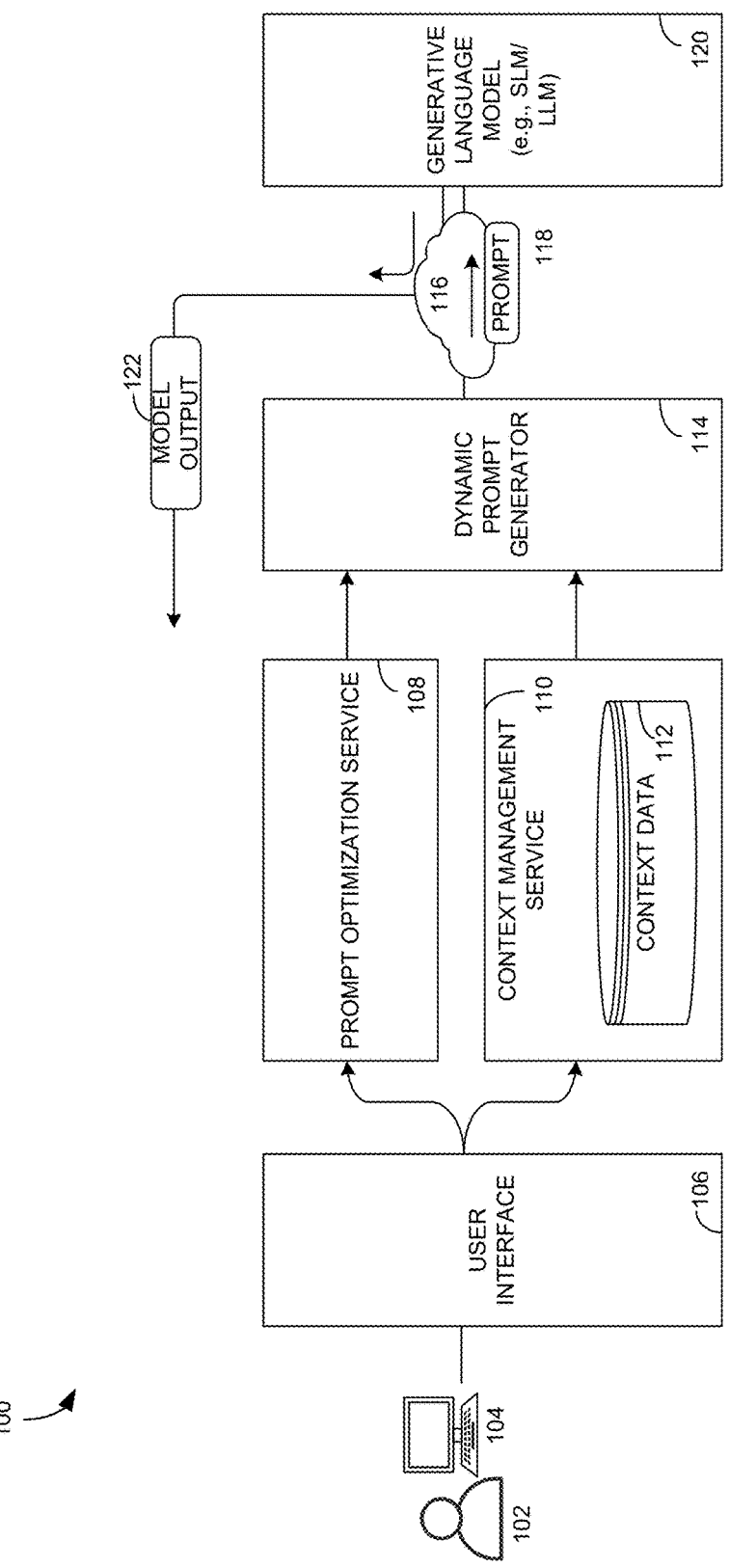
FIG. 1 illustrates a system architecture for generating optimized prompts using prompt optimization and context management services, showing components for dynamic prompt generation and interaction with generative language models, consistent with some embodiments.

Described herein are techniques for improving language model responses through automated prompt optimization and intelligent example selection. The methods and systems set forth herein enable precise control over prompt generation by using a multi-stage optimization process that combines automatically refined instructions with relevant historical examples. Rather than relying on static, manually-designed prompts that may provide suboptimal results, the disclosed approaches allow systems to dynamically generate and optimize prompts through iterative mutation and refinement operations while incorporating semantically similar examples retrieved through vector similarity search. The system combines optimized prompt instructions generated through controlled mutation operations with carefully selected historical examples and contextual information to improve response quality across various applications. In the following description, numerous specific details are provided, including techniques for prompt optimization, methods for similarity-based example retrieval, and approaches for combining optimized instructions with relevant context. These details enable one skilled in the art to practice the disclosed embodiments. It will be apparent, however, to one skilled in the art that the disclosed embodiments may be practiced without these specific details.

Conventional approaches to using generative language models (e.g., large language models, or LLMs) for complex tasks face significant technical challenges in providing accurate and efficient responses. These systems typically rely on static, manually designed prompts that lack the flexibility to adapt as tasks and models evolve, making continual updates labor-intensive and leading to sub-optimal performance. The conventional approach requires significant manual effort from domain experts to craft prompts, which often fail to fully leverage the potential of underlying language models.

These static prompts present two distinct technical problems. First, manually defined prompts lack the flexibility to adapt as tasks and models evolve, making maintenance and updates labor-intensive. Second, these static prompts may not fully leverage the language model's potential, leading to sub-optimal recommendations without automated optimization. Additionally, when examples are included with static prompts, they may not provide the most relevant context for the specific task being analyzed, further degrading response quality.

The limitations of conventional approaches are particularly evident in systems that rely on either default fine-tuning or retrieval augmented generation (RAG) methods with static, manually designed prompts. These systems struggle to maintain consistent performance as underlying models evolve and new variations of tasks emerge. The static nature of these prompts prevents the system from adapting to new patterns or incorporating learned improvements over time.

Furthermore, existing systems face challenges in efficiently combining prompt instructions with relevant historical examples. Traditional approaches either include too many examples, increasing computational overhead, or too few examples, limiting the context available for accurate response generation. The selection and integration of examples with prompt instructions often relies on manual curation, leading to inconsistent performance across different use cases.

These technical challenges stem from the fundamental limitations of static prompt engineering approaches, which cannot effectively balance the competing needs for adaptability, efficiency, and response quality. Conventional systems either rely too heavily on expensive large language models, making deployment at scale prohibitively costly, or use smaller models without proper optimization, resulting in degraded performance.

The limitations of static prompts become particularly evident when examining specific use cases. In root cause analysis for network- and cloud-based systems, for example, a static prompt fails to adapt to the diverse nature of operational incidents. When analyzing a network connectivity issue, the same generic prompt used for analyzing a database performance problem provides sub-optimal guidance to the generative language model, potentially missing critical domain-specific patterns and relationships. This leads to incomplete or inaccurate root cause identification, delaying incident resolution and extending service disruptions.

In medical diagnosis scenarios, static prompts face similar challenges. When analyzing patient cases, a fixed prompt cannot effectively adapt to the varying complexity and interconnected nature of symptoms, medical history, and test results. For instance, the same static prompt used to analyze cardiac symptoms may fail to properly guide the model when examining neurological conditions, leading to potentially missed diagnostic patterns or inappropriate treatment recommendations.

The technical limitations are equally problematic in code debugging applications. A static prompt used to analyze memory leaks may lack the specific instruction patterns needed to effectively guide the model when examining race conditions or API integration issues. Without dynamic optimization, the prompt fails to incorporate relevant debugging patterns learned from similar historical cases, resulting in incomplete bug identification or ineffective fix recommendations.

These use cases highlight a common technical problem: static prompts cannot effectively capture the context-specific nuances required for accurate analysis. In root cause analysis, this manifests as delayed incident resolution; in medical diagnosis, it results in potentially missed diagnostic patterns; and in code debugging, it leads to incomplete problem identification. The static nature of these prompts prevents the system from leveraging valuable patterns and relationships identified in similar historical cases, significantly limiting the effectiveness of the underlying language models.

Furthermore, when these static prompts are combined with example selection, additional technical challenges emerge. In root cause analysis, relevant historical incidents may be overlooked if the prompt doesn't effectively guide the similarity matching process. In medical diagnosis, critical case histories might be missed due to suboptimal prompt construction. In debugging scenarios, valuable code fix patterns may not be properly identified and incorporated. These limitations compound the fundamental problem of static prompts, further degrading system performance across all use cases.

Set forth herein is a novel approach for dynamically optimizing language model responses through an integrated system that combines automated prompt refinement with intelligent context retrieval. The disclosed system provides a novel technical solution for improving generative language model responses through automated prompt optimization and intelligent example selection. At a high level, the system combines three key technical components that work together to generate optimized prompts: (1) automated prompt instruction optimization, (2) intelligent historical example retrieval, and (3) dynamic prompt assembly.

The first component leverages a prompt optimization system that performs a one-time optimization process during training to generate an optimized prompt instruction. This prompt optimization system takes an initial prompt instruction and applies mutation operations using a first generative language model to generate multiple variations. A second generative language model acts as a critic, evaluating these variations and providing targeted feedback. Through iterative refinement based on this feedback, the system converges on an optimized prompt instruction that better guides the underlying language model. Once generated, this optimized prompt instruction remains fixed during inference operations.

The second component implements an intelligent example retrieval system using vector similarity search that operates during inference. The system maintains a vector database of historical examples, pre-encoded as embedding vectors using a sentence transformer model. When processing a new task, the system dynamically encodes the task context data into a vector representation and uses a similarity search engine to compute distance metrics between this vector and the stored example vectors. This enables efficient identification and retrieval of the most semantically similar historical examples at runtime.

The third component assembles the final prompt by combining the pre-computed optimized instruction with dynamically retrieved examples and current task context during inference. This assembly process ensures that each prompt is tailored to the specific task while leveraging both the optimized instruction and relevant historical patterns.

The system can be configured to include a predetermined number of the most similar historical examples, balancing the need for comprehensive context against computational efficiency.

The system maintains efficiency through several key mechanisms. The prompt optimization process is executed only once during training, using a single language model call for generating mutations while limiting total optimization iterations. During inference, the system uses the fixed optimized prompt instruction, avoiding repeated optimization costs. The vector similarity search enables fast retrieval of relevant examples without exhaustive comparison. The system can also work with smaller, fine-tuned language models for production deployment while maintaining performance through the pre-computed optimized prompts.

This technical solution is applicable across various domains. In root cause analysis, the system optimizes prompts to better guide analysis of operational incidents while retrieving similar historical incidents for context. In medical diagnosis, it refines prompts for analyzing patient cases while incorporating relevant case histories. In code debugging, it optimizes prompts for analyzing software issues while leveraging patterns from similar historical bugs.

The system's configurable parameters enable fine-tuned control over the optimization process, including the number of mutation rounds, mutations per round, evaluation batch size, and minimum performance thresholds. This allows organizations to balance optimization quality against computational resources based on their specific needs.

In addition to the prompt optimization and example retrieval capabilities, consistent with some embodiments, the system enables efficient deployment through the use of smaller language models that can be fine-tuned for specific domains. For example, in one implementation, the system may fine-tune compact language models using hundreds of thousands of historical examples across thousands of different services. The training process may utilize various optimization techniques, such as weight decay and learning rate scheduling with warm-up phases, to enhance model performance and prevent overfitting.

These fine-tuned compact models can provide substantial advantages compared to larger alternatives. While maintaining comparable performance through the optimized prompts described herein, such generative language models may require significantly reduced computational resources—in some implementations operating at a fraction of the cost of larger models while achieving similar results on evaluation benchmarks. For instance, models developed using several billion parameters and curated training data can offer an efficient alternative to larger models trained on broader datasets.

When combined with the prompt optimization system described above, fine-tuned models have shown significant improvements in accuracy compared to baseline approaches using context alone. Such performance gains, coupled with reduced computational requirements, make these smaller models particularly well-suited for continuous monitoring and real-time analysis in production environments where efficiency and cost considerations are important factors. Other aspects and advantages of the various embodiments of the innovative systems set forth herein will be readily apparent from the detailed descriptions of the several drawings that follows.

FIG. 1 illustrates a system architecture 100 for generating optimized input prompts, for use as the input to a generative language model, using prompt optimization and context management services, showing components for dynamic prompt generation and interaction with generative language models, consistent with some embodiments. As illustrated in FIG. 1, a user 102 interacting with a computing system 104, access the system through a user interface 106. In various embodiments, the user interface 106 may be implemented differently depending on the specific application. For example, in some implementations, the interface may provide forms for entering task descriptions and an initial prompt instruction. In other implementations, it may offer pre-configured options and templates that automatically generate an appropriate initial instruction when selected. For example, in a root cause analysis implementation, when the system detects an operational incident through monitoring services, a notification may be sent to an on-call engineer's device, where selecting a "Analyze Root Cause" button automatically triggers the system to use a pre-configured prompt instruction tailored for that specific type of incident.

In operation, when a user submits a task through the interface 106, the system processes the request through both the prompt optimization service 108 and context management service 110 in parallel. The prompt optimization service 108 works to optimize the instruction portion of the prompt, while the context management service 110 identifies and retrieves relevant historical examples from its context data 112.

Accordingly, the system architecture comprises three primary components that operate together to generate optimized prompts for improving language model responses. The prompt optimization service 108 receives task context data and an initial prompt instruction, then employs multiple generative language models to iteratively refine the instruction through controlled mutation and evaluation cycles. A first generative model generates prompt variations through mutation operations, while a second model acts as a critic to evaluate and provide feedback on these variations. Through this iterative process, the system converges on an optimized prompt instruction that better guides the underlying model in performing the specified task.

The context management service 110 implements an intelligent example retrieval system that enables in-context learning by providing relevant historical examples to guide the language model's reasoning. The service maintains a vector database of historical examples that are pre-encoded as embedding vectors using a sentence transformer model. When processing a new task, the service encodes the task context data into a vector representation and uses a similarity search engine to compute distance metrics between this vector and the stored example vectors. This enables efficient identification and retrieval of the most semantically similar historical examples that can inform the current task. The retrieved examples provide valuable domain-specific context and enable pattern recognition across similar situations.

The dynamic prompt generator 114 assembles the final prompt 118 by combining three key elements: the optimized prompt instruction from the prompt optimization service, a predetermined number of the most similar historical examples identified by the context management service 110, and the current task context data. This assembly process ensures that each prompt is tailored to the specific task while leveraging both optimized instructions and relevant historical patterns. The dynamic prompt generator 114 structures these elements to maximize the language model's ability to understand the task requirements and generate accurate, contextually appropriate responses. The final prompt 118 is then provided to the generative language model 120, which may be implemented as either a large language model (LLM) or a smaller, fine-tuned model (SLM) depending on deployment requirements.

The system architecture enables flexible deployment across various use cases while maintaining a consistent approach to prompt optimization. Whether analyzing system incidents for root cause analysis, medical cases, or code issues, the primary components operate together to generate high-quality prompts that improve model outputs while maintaining computational efficiency.

The system can be implemented across diverse applications by adapting the prompt optimization and context management services to different domains while maintaining the core architecture. For example, the system can be configured for medical diagnosis by incorporating medical knowledge bases, for code debugging by integrating with development environments, or for root cause analysis by connecting to system monitoring tools. This flexibility allows organizations to leverage the same underlying prompt optimization capabilities while tailoring the implementation to their specific needs.

In a root cause analysis implementation, the user interface 106 may be integrated with monitoring dashboards and system telemetry displays that provide real-time visibility into the operational status of cloud services and infrastructure components. The interface continuously displays key performance metrics, error rates, and system health indicators collected from various monitoring services. When anomalies or potential issues are detected, the interface highlights the affected components and surfaces relevant telemetry data, such as increased error rates, latency spikes, or resource utilization changes.

The user interface 106 provides interactive visualization capabilities that allow engineers to explore the system state and drill down into specific metrics or logs. When an incident occurs, the affected metrics and components are automatically highlighted, and the interface presents an "Analyze Root Cause" button or similar action element. When an engineer selects this button, the system automatically captures the current system state and telemetry data, which is then used to select an appropriate initial prompt instruction from a library of pre-configured prompts based on the type and characteristics of the detected incident.

This selected initial prompt instruction is then provided to the prompt optimization service for refinement and optimization through controlled mutation and evaluation cycles. The captured incident information and selected prompt are used to automatically initiate the root cause analysis process, with the system retrieving relevant historical examples and generating an optimized prompt through the system's prompt optimization and context management services. The interface then displays the analysis progress and ultimately presents the identified root causes, supporting evidence, and recommended mitigation steps in an intuitive format that helps engineers quickly understand and act on the findings.

For root cause analysis scenarios, the context management service 110 maintains a specialized database of historical incidents, including verified root causes documented by engineers, configuration changes, performance metrics, and troubleshooting guides. The context data 112 is organized to enable efficient retrieval of relevant historical incidents based on similarities in error patterns, system behaviors, and service dependencies.

When processing an incident, the prompt optimization service 108 generates instructions specifically designed to guide the language model in analyzing system logs, identifying error patterns, and determining root causes. The dynamic prompt generator 114 combines these optimized instructions with the most relevant historical incidents that share similar characteristics with the current case.

The system provides specialized visualization capabilities through the user interface 106 to help engineers understand the relationship between the current incident and historical cases. This includes displaying key metadata, error patterns, and system metrics that contributed to identifying similar incidents. The interface may also provide options for engineers to provide feedback on the generated root cause analysis, helping to continuously improve the system's performance.

The generative language model 120 receives the optimized prompt containing both the refined instructions and relevant historical examples, enabling it to leverage patterns from similar past incidents while maintaining focus on the specific characteristics of the current case. The model output 122 includes not only the identified root cause but also supporting evidence from logs and metrics, along with recommended mitigation steps based on successful resolutions of similar historical incidents.

In a medical diagnosis implementation, the user interface 106 may be configured to receive and display comprehensive patient information through multiple input mechanisms. In some implementations, clinicians may manually enter detailed patient data through specialized forms. In other implementations, the interface may automatically import data from electronic health records or medical devices. The system may also present an "Analyze Diagnosis" button when sufficient patient data is available, which when selected, automatically generates or selects an appropriate initial prompt instruction based on the type and characteristics of the presented symptoms and test results.

For medical applications, the context management service 110 maintains a specialized database 112 containing historical medical cases, including verified diagnoses, treatment outcomes, clinical notes, and relevant medical reference documentation. The context data is organized using vector embeddings to enable efficient retrieval of similar cases based on symptom patterns, test results, and other clinical parameters. This allows the system to identify and leverage patterns from historical cases that share characteristics with the current patient's presentation.

When processing a medical case, the prompt optimization service 108 takes the initial prompt instruction—whether manually entered by the clinician or automatically selected based on the case characteristics—and refines it through controlled mutation and evaluation cycles. The dynamic prompt generator 114 then combines the optimized prompt instruction with the most relevant historical cases to create a comprehensive prompt that guides the generative language model 120 in analyzing the specific medical case.

The system provides specialized medical visualization capabilities through the user interface 106 to help clinicians understand the diagnostic reasoning process. The interface displays the relationships between the current case and similar historical cases, highlighting key clinical parameters, test results, and treatment outcomes that influenced the analysis. Clinicians can provide feedback on the generated diagnoses through the interface, which helps continuously improve the system's diagnostic accuracy and prompt optimization process.

The model output 122 provides comprehensive diagnostic information including proposed diagnoses with associated confidence levels, supporting clinical evidence and reasoning chains, references to similar historical cases that informed the analysis, recommended additional diagnostic tests, and suggested treatment options based on successful outcomes from similar cases. The system structures this output to help clinicians quickly understand the diagnostic reasoning and make informed treatment decisions.

The system maintains strict patient privacy and security protocols while enabling efficient access to relevant historical cases that can inform current diagnostic decisions. The combination of optimized prompts and carefully selected historical examples helps guide the language model in generating accurate, clinically relevant, and well-supported diagnostic recommendations that consider both the specific details of the current case and patterns identified from similar historical cases.

In a code debugging implementation, the user interface 106 may be integrated directly into integrated development environments (IDEs) and code editors, enabling developers to access debugging assistance without leaving their development workflow. The interface provides specialized components for displaying code snippets, error messages, stack traces, and execution logs in real-time as developers write and test code. When potential issues are detected through static analysis or runtime errors, the interface automatically highlights the problematic code sections and provides contextual debugging suggestions.

For debugging applications, the context management service 110 maintains a specialized database 112 containing historical debugging cases, common code patterns and anti-patterns, verified bug fixes, test results, and documentation references. The context data is organized using vector embeddings to enable efficient retrieval of similar cases based on error patterns, code structure, and execution behavior. This allows the system to identify and leverage debugging patterns from historical cases that share characteristics with the current issue.

When a developer encounters an error or selects problematic code, they can trigger analysis directly through the IDE interface. The system automatically captures the relevant code context, error messages, and execution state to select an appropriate initial prompt instruction from a library of debugging-focused prompts. This initial prompt is then provided to the prompt optimization service 108 for refinement through controlled mutation and evaluation cycles specifically designed for code analysis tasks.

The system provides specialized debugging visualization capabilities through deep IDE integration. Developers can view side-by-side comparisons between their current code and similar historical bugs, examine relevant code patterns identified from the database, and understand dependencies between different components. The interface tracks the impact of suggested fixes and allows developers to validate changes against patterns from successfully resolved historical cases.

The model output 122 provides comprehensive debugging information including detailed analysis of identified issues, supporting evidence from logs and execution traces, references to similar bug patterns from the database, and specific code fix recommendations. The system also generates impact analysis for suggested changes, helping developers understand potential side effects before implementing fixes.

The seamless integration with development environments enables developers to maintain their existing workflow while leveraging the system's capabilities. They can trigger analysis, review suggestions, apply recommended fixes, and document resolutions without context switching between different tools. This integration, combined with the system's ability to learn from historical debugging patterns, helps accelerate the bug identification and resolution process while maintaining code quality.

Figure 2:
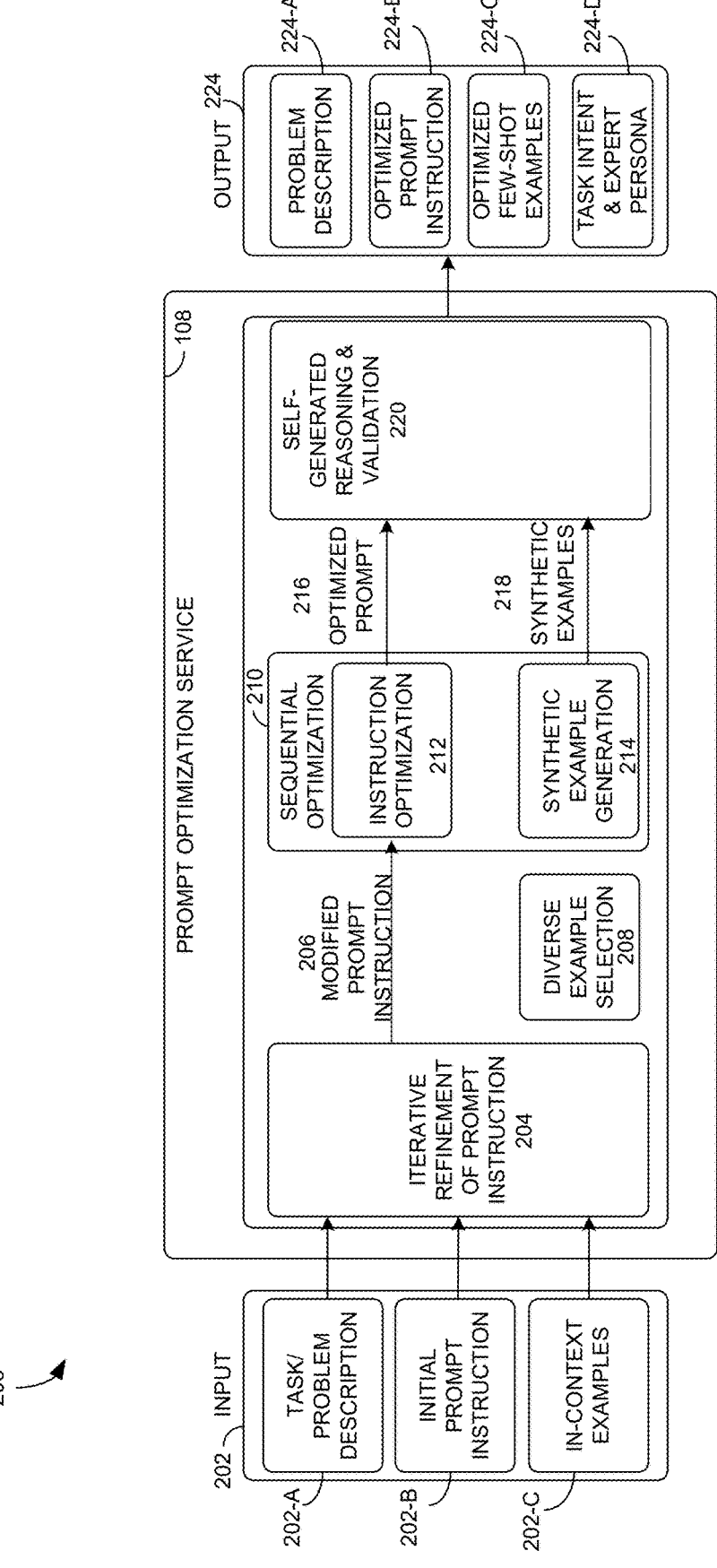
FIG. 2 illustrates internal components of a prompt optimization service, showing the flow from input task descriptions through iterative refinement to generate optimized prompts and examples, consistent with some embodiments.

FIG. 2 illustrates internal components of a prompt optimization service, showing the flow from input task descriptions through iterative refinement to generate optimized prompts and examples, consistent with some embodiments. As shown in FIG. 2, the prompt optimization service 108 receives three key inputs 202: a task/problem description 202-A describing the task to be performed, an initial prompt instruction 202-B for guiding the generative language model, and optionally, in-context examples 202-C that provide relevant examples for the task. These inputs undergo iterative refinement 204 through a multi-stage optimization process.

While FIG. 2 illustrates one example implementation of the prompt optimization service 108, alternative implementations may vary in their specific inputs and processing steps. For example, in some implementations, the service may operate with only an initial prompt instruction 202-B as input, without requiring additional task descriptions or examples. The iterative refinement and optimization processes may also be configured differently based on specific requirements, such as adjusting the number of mutation rounds or evaluation criteria. Additionally, the output components 224-A through 224-D may be selectively included or omitted depending on the particular use case and implementation needs.

In the iterative refinement stage 204, a first generative language model (not shown) generates multiple variations of the initial prompt instruction through controlled mutation operations. These mutations are generated in a single language model call to maintain efficiency. A second generative language model (not shown) acts as a critic, evaluating each variation and assigning performance-based scores using training samples. The best-performing variation is selected for further refinement based on targeted feedback from the critic model.

The selected prompt variation proceeds through sequential optimization 210, which includes instruction optimization 212 and synthetic example generation 214. During instruction optimization, the system continues to refine the prompt through multiple rounds of mutation and evaluation until reaching a configured convergence criterion or maximum iteration count. The number of mutation rounds, mutations per round, and evaluation batch size are configurable parameters that allow organizations to balance optimization quality with computational efficiency.

The synthetic example generation component 214 can create diverse example cases that complement the optimized instruction. These synthetic examples may be used directly in the final prompt, or in some implementations, may be replaced by semantically similar historical examples retrieved through the context management service 110. The system maintains efficiency by limiting the total number of language model calls during both instruction optimization and example generation.

The configurable parameters directly control the computational resources and costs associated with the prompt optimization process. For example, if the number of mutation rounds is set to 3, mutations per round is set to 5, and evaluation batch size is 10, this would result in:

3 rounds×5 mutations=15 total mutations generated by the first LLM 15 mutations×10 evaluations=150 total evaluations performed by the critic LLM.

Total of 165 LLM calls for the core optimization process

In some embodiments, the system includes functionality to estimate computational costs based on these parameters before beginning optimization. For example, when configured with:

mutate_refine_iterations: 3
    mutation_rounds: 3
    questions_batch_size: 5
    min_correct_count: 3
    The system can calculate that approximately 45-60 LLM API calls will be required to complete the optimization process.

This allows organizations to make informed decisions about the tradeoff between optimization quality and computational cost. Higher numbers of mutations and evaluation batches provide more opportunities to discover optimal prompts but increase the total number of LLM calls. The system maintains efficiency by using a single LLM call to generate multiple mutations in each round rather than separate calls for each mutation.

The optimization process incorporates self-generated reasoning and validation 220 to prevent errors and hallucination in the generated content. The final output 224 includes multiple components that can be selectively used based on implementation requirements: a problem description 224-A that frames the task, the optimized prompt instruction 224-B that guides the model, optimized few-shot examples 224-C for providing context, and optionally, task intent and expert persona elements 224-D that help maintain consistency and relevance.

The system's modular architecture allows different components of the output to be used flexibly depending on the specific use case. For example, in implementations where dynamic example retrieval is preferred, the optimized few-shot examples 224-C may be replaced with semantically similar historical examples from the context management service. Similarly, the task intent and expert persona 224-D can be included or omitted based on whether role-specific guidance is beneficial for the particular application.

Figure 3:
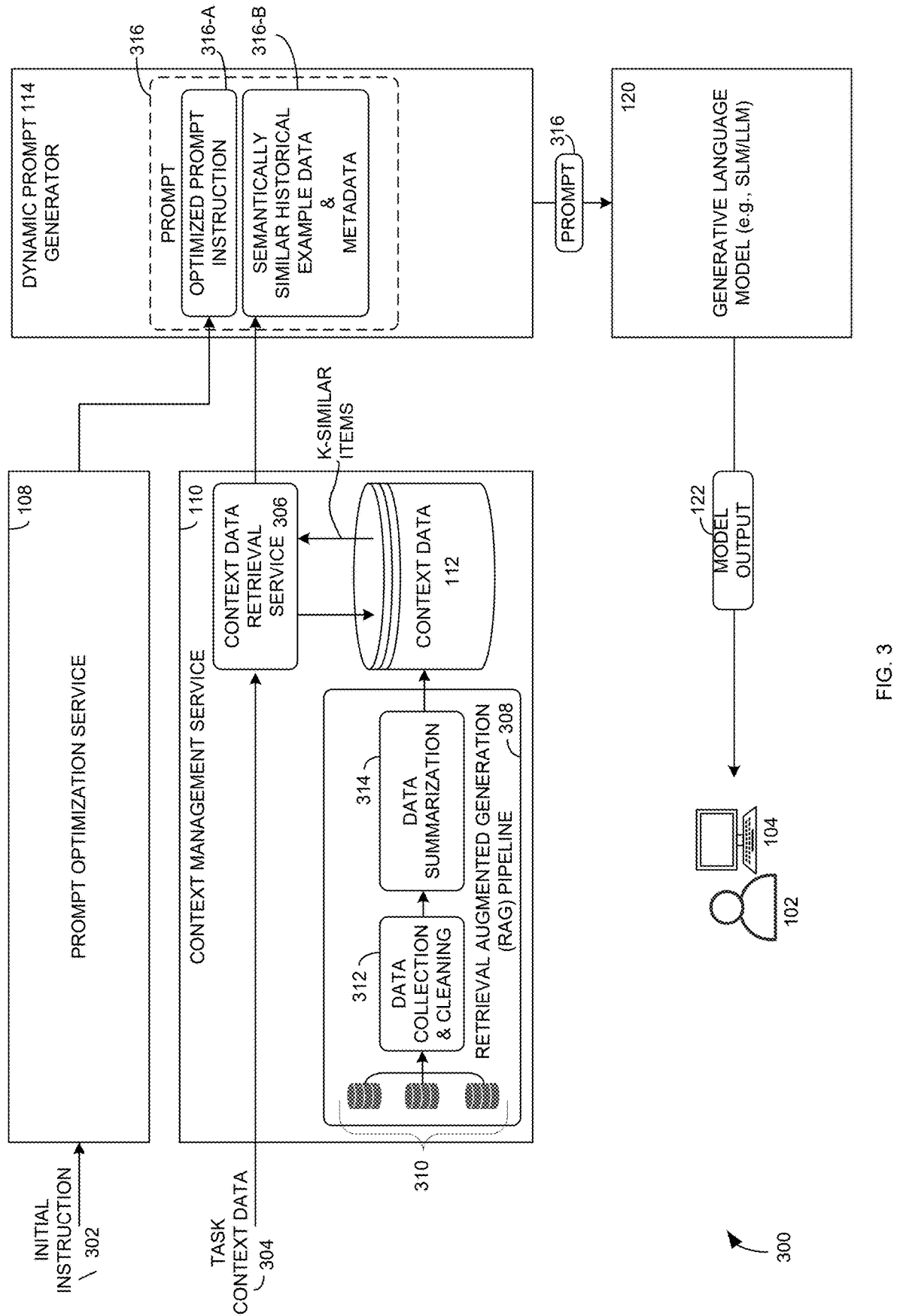
FIG. 3 illustrates a detailed system architecture incorporating retrieval augmented generation (RAG) capabilities, showing how context data is processed and combined with optimized prompts, consistent with some embodiments.

FIG. 3 illustrates a detailed system architecture 300 incorporating retrieval augmented generation (RAG) capabilities, showing how context data is processed and combined with optimized prompt instructions, consistent with some embodiments. As shown in FIG. 3, the prompt optimization service 108 receives an initial prompt instruction 302, while the context management service 110 receives task context data 304 that varies based on the specific use case.

For root cause analysis implementations, the task context data 304 may include incident titles, service identifications, error messages, system logs, and environment parameters. In medical diagnosis scenarios, the context data may comprise patient symptoms, vital signs, test results, and medical history. For code debugging applications, the context data typically includes error messages, stack traces, code snippets, and execution logs. Consistent with various other embodiments and implementations, the structure and content of the task context data 304 may be adapted and configured based on the specific requirements and characteristics of the particular use case or application domain.

The context management service 110 processes historical data 310 through a retrieval augmented generation (RAG) pipeline 308 to build and maintain the context data 112. The data collection & cleaning component 312 preprocesses the raw historical data to remove extraneous information such as HTML tags, images, stack traces, and code snippets that could interfere with similarity matching. For example, in root cause analysis scenarios, the cleaning process removes irrelevant technical logs while preserving key incident details.

The data summarization component 314 then processes the cleaned data using a generative language model (e.g., GPT-3.5-turbo) to create concise summaries that capture essential information while reducing overall length. The summarization process is guided by prompts that ensure key elements are preserved—for example, in incident data, the summaries retain information about symptoms, external service references, error codes, and contextual details like service names. This summarization step helps filter out noise and standardize the data format while maintaining critical context.

The summarized data is then encoded into vector embeddings using a sentence transformer model and stored in the context data 112. When processing a new task, the context data retrieval service 306 receives task context data 304 and similarly encodes it into a vector representation. The service then computes distance metrics between this query vector and the stored embeddings to identify some number of the most semantically similar historical examples, and associated metadata.

Consistent with some embodiments, the similarity search uses the FAISS (Facebook® AI Similarity Search) library to efficiently compute L2 (Euclidean) distance metrics between the vectors. This enables fast retrieval of relevant examples even when searching across large datasets, as FAISS uses compressed vector representations that can handle billions of vectors in memory on a single server. The system retrieves a configurable number (K) of the most similar items based on these distance calculations. Of course, any of a number of other distance metrics may be used in alternative embodiments.

The retrieved K-similar items are combined with their associated metadata and provided to the dynamic prompt generator 114 along with the optimized prompt instruction 316-A to form the final prompt 316. This ensures that each generated prompt includes both optimized instructions and the most relevant historical context for the specific task being performed.

The model output 122 is communicated to the user 102 through the computing system 104 via one or more networks 580 using various communication components 564 such as wired, wireless, cellular, or Wi-Fi connections. The communication components enable secure and efficient transmission of the generated responses, recommendations, and supporting evidence from the generative language model 120 to the user's device.

The generative language model 120 may be implemented using various types of models depending on deployment requirements and computational constraints. In some embodiments, the system may utilize large language models (LLMs) accessed over a network from model providers, which offer extensive capabilities but higher computational costs. In other embodiments, the system may leverage open source models that can be deployed locally. Additionally, the system enables the use of smaller, fine-tuned language models (SLMs) that are optimized for specific domains while maintaining efficiency.

The system's ability to work with different types of models provides flexibility in balancing performance and cost requirements. For example, organizations may use larger models during development and testing, then transition to optimized SLMs for production deployment. The system's prompt optimization capabilities help maintain high-quality outputs regardless of the underlying model choice.

In various embodiments, the system includes functionality for fine-tuning smaller language models for specific domains and applications. At a high level, the fine-tuning process involves training a pre-trained model on domain-specific data to adapt it for particular tasks while maintaining general language understanding capabilities. This approach enables more efficient deployment compared to larger models while maintaining comparable performance through optimized prompts.

For example, in one implementation, the system fine-tunes compact language models using hundreds of thousands of historical examples across thousands of different services. The training process allocates a portion of the historical data for validation (e.g., 10,000 examples) and testing (e.g., 3,000 examples), with the remainder used for training. A temporal split may be employed, with older data used for training and newer cases for testing, to simulate real-world deployment scenarios.

The fine-tuning process may utilize various optimization techniques to enhance model performance and prevent overfitting. For instance, the system may employ the AdamW optimizer with weight decay and implement a linear learning rate scheduler with warm-up phases. The training may be performed over multiple epochs using compute clusters with specialized hardware such as GPU arrays. These fine-tuned models can achieve significant improvements in accuracy compared to baseline approaches while requiring substantially reduced computational resources—in some implementations operating at a fraction of the cost of larger models.

The various embodiments described herein provide several significant technical advantages. First, by automatically optimizing prompt instructions through controlled mutation and evaluation cycles, the system eliminates the need for manual prompt engineering while consistently improving response quality as language models evolve. Second, the vector-based similarity search enables efficient retrieval of relevant historical examples without exhaustive comparison, significantly reducing computational overhead compared to traditional approaches.

Third, the system's ability to work with smaller, fine-tuned language models provides substantial cost savings in production environments while maintaining high-quality performance through optimized prompts. For example, implementations using compact models with 3-15 billion parameters can operate at a fraction of the cost of larger models while achieving comparable results on evaluation benchmarks.

Fourth, the system's modular architecture enables flexible deployment across diverse applications while maintaining a consistent approach to prompt optimization. Whether analyzing system incidents, medical cases, or code issues, organizations can leverage the same underlying optimization capabilities while tailoring the implementation to their specific needs. This flexibility, combined with configurable parameters for controlling computational resources, allows organizations to effectively balance optimization quality against operational costs.

Machine and Software Architecture

Figure 4:
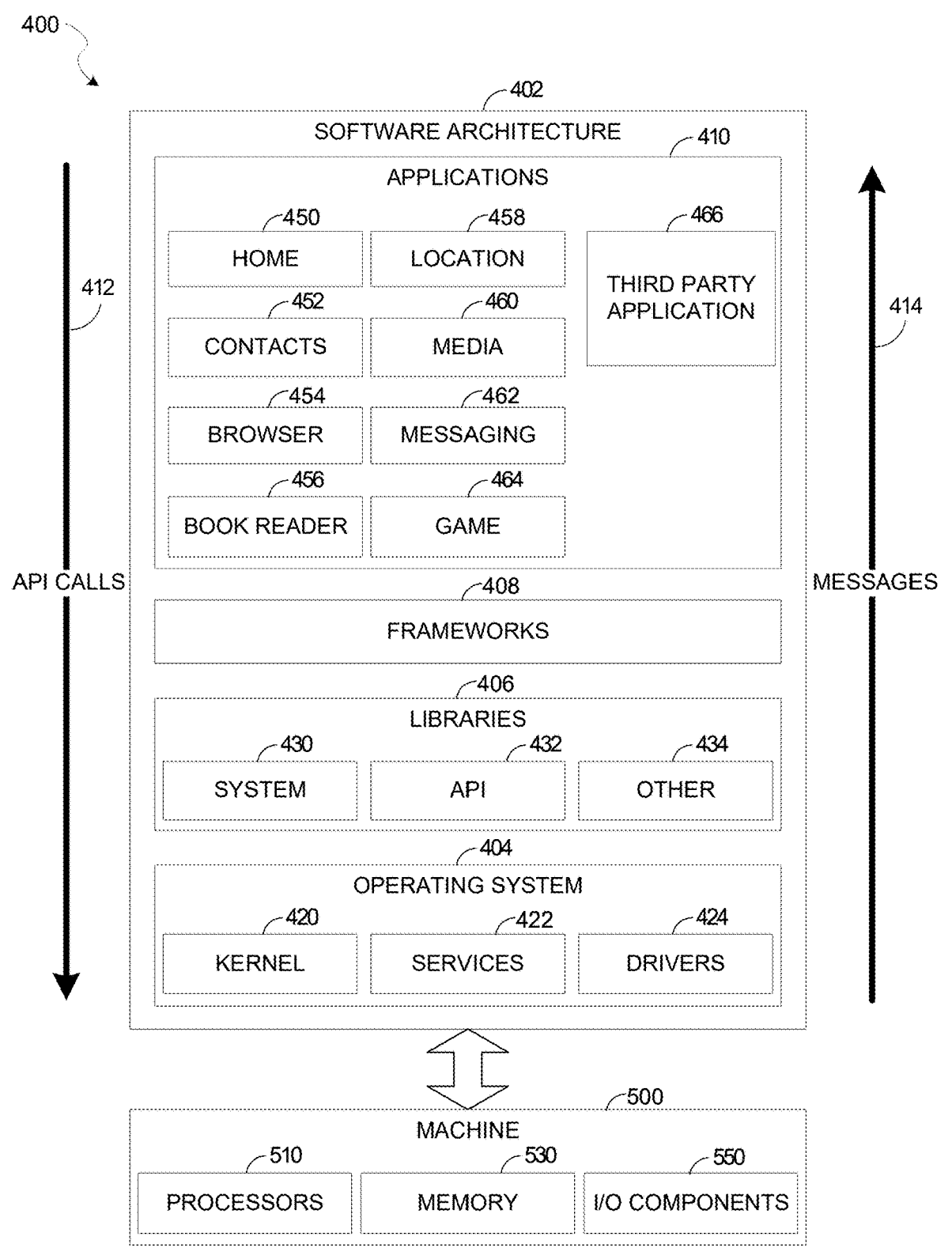
FIG. 4 illustrates a software architecture that may be installed on a machine for implementing the prompt optimization system, consistent with some embodiments.

FIG. 4 is a block diagram 400 illustrating a software architecture 402, which can be installed on any of a variety of computing devices to perform methods consistent with those described herein. FIG. 4 is merely a non-limiting example of a software architecture, and it will be appreciated that many other architectures can be implemented to facilitate the functionality described herein. In various embodiments, the software architecture 402 is implemented by hardware such as a machine 500 of FIG. 5 that includes processors 510, memory 530, and input/output (I/O) components 550. In this example architecture, the software architecture 402 can be conceptualized as a stack of layers where each layer may provide a particular functionality. For example, the software architecture 402 includes layers such as an operating system 404, libraries 406, frameworks 408, and applications 410. Operationally, the applications 410 invoke API calls 412 through the software stack and receive messages 414 in response to the API calls 412, consistent with some embodiments.

In various embodiments, the operating system 404 manages hardware resources and provides common services. The operating system 404 includes, for example, a kernel 420, services 422, and drivers 424. The kernel 420 acts as an abstraction layer between the hardware and the other software layers, consistent with some embodiments. For example, the kernel 420 provides memory management, processor management (e.g., scheduling), component management, networking, and security settings, among other functionality. The services 422 can provide other common services for the other software layers. The drivers 424 are responsible for controlling or interfacing with the underlying hardware, according to some embodiments. For instance, the drivers 424 can include display drivers, camera drivers, BLUETOOTH® or BLUETOOTH® Low Energy drivers, flash memory drivers, serial communication drivers (e.g., Universal Serial Bus (USB) drivers), Wi-Fi® drivers, audio drivers, power management drivers, and so forth.

In some embodiments, the libraries 406 provide a low-level common infrastructure utilized by the applications 410. The libraries 406 can include system libraries 430 (e.g., C standard library) that can provide functions such as memory allocation functions, string manipulation functions, mathematic functions, and the like. In addition, the libraries 406 can include API libraries 432 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic context on a display), database libraries (e.g., SQLite to provide various relational database functions), web libraries (e.g., WebKit to provide web browsing functionality), and the like. The libraries 406 can also include a wide variety of other libraries 434 to provide many other APIs to the applications 410.

The frameworks 408 provide a high-level common infrastructure that can be utilized by the applications 410, according to some embodiments. For example, the frameworks 408 provide various GUI functions, high-level resource management, high-level location services, and so forth. The frameworks 408 can provide a broad spectrum of other APIs that can be utilized by the applications 410, some of which may be specific to a particular operating system 404 or platform.

In an example embodiment, the applications 410 include a home application 450, a contacts application 452, a browser application 454, a book reader application 456, a location application 458, a media application 460, a messaging application 462, a game application 464, and a broad assortment of other applications, such as a third-party application 466. According to some embodiments, the applications 410 are programs that execute functions defined in the programs. Various programming languages can be employed to create one or more of the applications 410, structured in a variety of manners, such as object-oriented programming languages (e.g., Objective-C, Java, or C++) or procedural programming languages (e.g., C or assembly language). In a specific example, the third-party application 466 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 466 can invoke the API calls 412 provided by the operating system 404 to facilitate functionality described herein.

Figure 5:
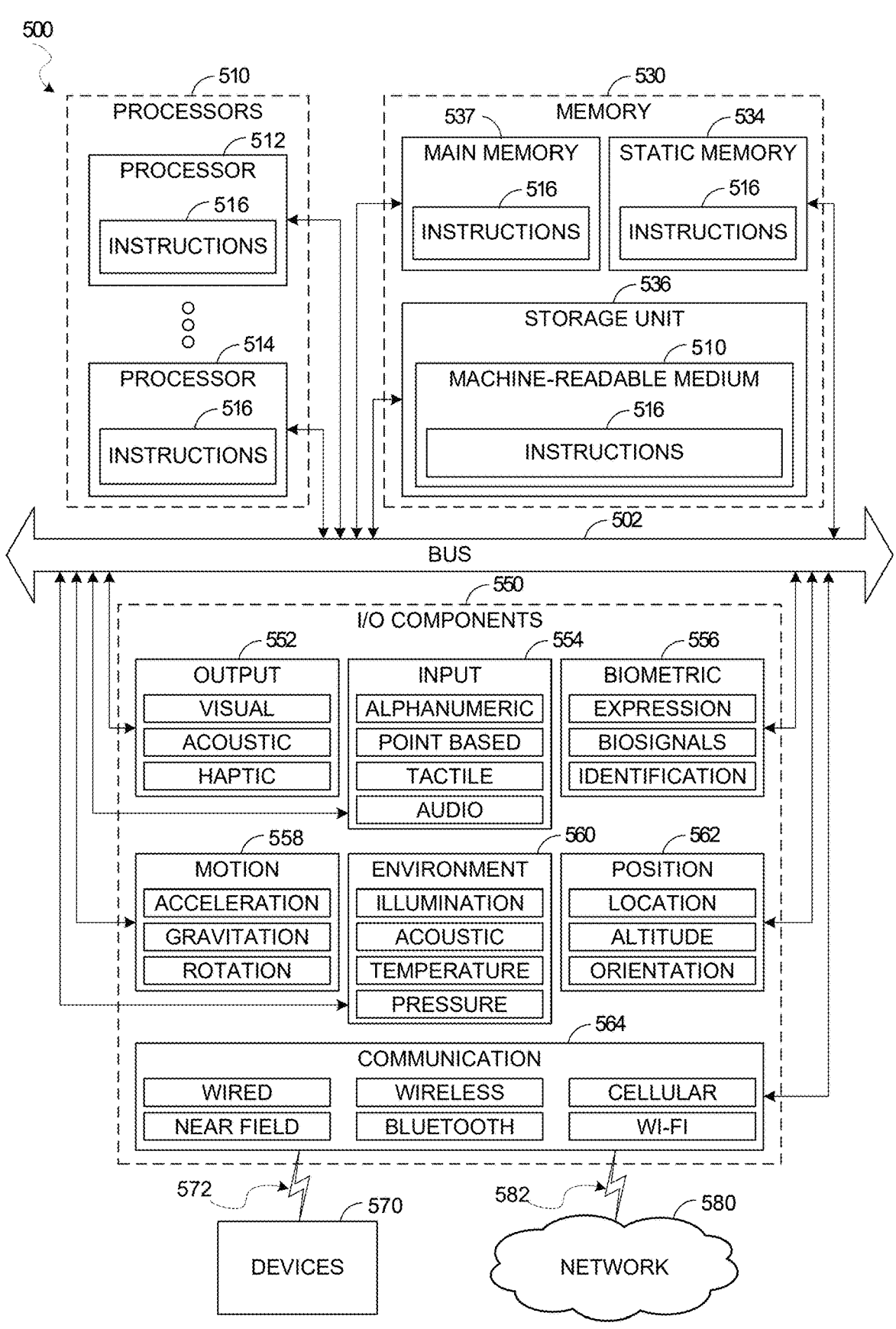
FIG. 5 illustrates a diagrammatic representation of machine components and I/O interfaces that may be used to implement the prompt optimization system, consistent with some embodiments.

FIG. 5 illustrates a diagrammatic representation of a machine 500 in the form of a computer system within which a set of instructions may be executed for causing the machine to perform any one or more of the methodologies discussed herein, according to an example embodiment. Specifically, FIG. 5 shows a diagrammatic representation of the machine 500 in the example form of a computer system, within which instructions 516 (e.g., software, a program, an application, an applet, an app, or other executable code) for causing the machine 500 to perform any one or more of the methodologies discussed herein may be executed. For example the instructions 516 may cause the machine 500 to execute any one of the methods or algorithmic techniques described herein. Additionally, or alternatively, the instructions 516 may implement any one of the systems described herein. The instructions 516 transform the general, non-programmed machine 500 into a particular machine 500 programmed to carry out the described and illustrated functions in the manner described. In alternative embodiments, the machine 500 operates as a standalone device or may be coupled (e.g., networked) to other machines. In a networked deployment, the machine 500 may operate in the capacity of a server machine or a client machine in a server-client network environment, or as a peer machine in a peer-to-peer (or distributed) network environment. The machine 500 may comprise, but not be limited to, a server computer, a client computer, a PC, a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 516, sequentially or otherwise, that specify actions to be taken by the machine 500. Further, while only a single machine 500 is illustrated, the term "machine" shall also be taken to include a collection of machines 500 that individually or jointly execute the instructions 516 to perform any one or more of the methodologies discussed herein.

The machine 500 may include processors 510, memory 530, and I/O components 550, which may be configured to communicate with each other such as via a bus 502. In an example embodiment, the processors 510 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 512 and a processor 514 that may execute the instructions 516. The term "processor" is intended to include multi-core processors that may comprise two or more independent processors (sometimes referred to as "cores") that may execute instructions contemporaneously. Although FIG. 5 shows multiple processors 510, the machine 500 may include a single processor with a single core, a single processor with multiple cores (e.g., a multi-core processor), multiple processors with a single core, multiple processors with multiples cores, or any combination thereof.

The memory 530 may include a main memory 532, a static memory 534, and a storage unit 536, all accessible to the processors 510 such as via the bus 502. The main memory 530, the static memory 534, and storage unit 536 store the instructions 516 embodying any one or more of the methodologies or functions described herein. The instructions 516 may also reside, completely or partially, within the main memory 532, within the static memory 534, within the storage unit 536, within at least one of the processors 510 (e.g., within the processor's cache memory), or any suitable combination thereof, during execution thereof by the machine 500.

The I/O components 550 may include a wide variety of components to receive input, provide output, produce output, transmit information, exchange information, capture measurements, and so on. The specific I/O components 550 that are included in a particular machine will depend on the type of machine. For example, portable machines such as mobile devices will likely include a touch input device or other such input mechanisms, while a headless server machine will likely not include such a touch input device. It will be appreciated that the I/O components 550 may include many other components that are not shown in FIG. 5. The I/O components 550 are grouped according to functionality merely for simplifying the following discussion and the grouping is in no way limiting. In various example embodiments, the I/O components 550 may include output components 552 and input components 554. The output components 552 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 554 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 550 may include biometric components 556, motion components 558, environmental components 560, or position components 562, among a wide array of other components. For example, the biometric components 556 may include components to detect expressions (e.g., hand expressions, facial expressions, vocal expressions, body gestures, or eye tracking), measure bio-signals (e.g., blood pressure, heart rate, body temperature, perspiration, or brain waves), identify a person (e.g., voice identification, retinal identification, facial identification, fingerprint identification, or electroencephalogram-based identification), and the like. The motion components 558 may include acceleration sensor components (e.g., accelerometer), gravitation sensor components, rotation sensor components (e.g., gyroscope), and so forth. The environmental components 560 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 562 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 550 may include communication components 564 operable to couple the machine 500 to a network 580 or devices 570 via a coupling 582 and a coupling 572, respectively. For example, the communication components 564 may include a network interface component or another suitable device to interface with the network 580. In further examples, the communication components 564 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 570 may be another machine or any of a wide variety of peripheral devices (e.g., a peripheral device coupled via a USB).

Moreover, the communication components 564 may detect identifiers or include components operable to detect identifiers. For example, the communication components 564 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 564, such as location via Internet Protocol (IP) geolocation, location via Wi-Fi® signal triangulation, location via detecting an NFC beacon signal that may indicate a particular location, and so forth.

Executable Instructions and Machine Storage Medium

The various memories (i.e., 530, 532, 534, and/or memory of the processor(s) 510) and/or storage unit 536 may store one or more sets of instructions and data structures (e.g., software) embodying or utilized by any one or more of the methodologies or functions described herein. These instructions (e.g., the instructions 516), when executed by processor(s) 510, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

Transmission Medium

In various example embodiments, one or more portions of the network 580 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 580 or a portion of the network 580 may include a wireless or cellular network, and the coupling 582 may be a Code Division Multiple Access (CDMA) connection, a Global System for Mobile communications (GSM) connection, or another type of cellular or wireless coupling. In this example, the coupling 582 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 516 may be transmitted or received over the network 580 using a transmission medium via a network interface device (e.g., a network interface component included in the communication components 564) and utilizing any one of a number of well-known transfer protocols (e.g., HTTP). Similarly, the instructions 516 may be transmitted or received using a transmission medium via the coupling 572 (e.g., a peer-to-peer coupling) to the devices 570. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 516 for execution by the machine 500, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Computer-Readable Medium

The terms "machine-readable medium," "computer-readable medium" and "device-readable medium" mean the same thing and may be used interchangeably in this disclosure. The terms are defined to include both machine-storage media and transmission media. Thus, the terms include both storage devices/media and carrier waves/modulated data signals.

What is claimed is:

1. A computer-implemented method for generating an input prompt for a generative language model, the method comprising:

receiving task context data for a task and an initial prompt instruction for instructing the generative language model to perform the task;

generating an optimized prompt instruction with a prompt optimization system that uses one or more generative language models to iteratively apply at least one mutation operation and at least one refinement operation to the initial prompt instruction, wherein:

the at least one mutation operation comprises:

generating multiple variations of the initial prompt instruction via a first call to a first generative language model, assigning performance-based scores to each variation based on training samples via a second call to a second generative language model, and selecting a best-performing variation based on the scores;

the at least one refinement operation comprises:

receiving targeted feedback from the second generative language model regarding strengths and weaknesses of the best-performing variation, modifying the best-performing variation based on the received targeted feedback via a third call to a third generative language model to generate a modified prompt instruction, and repeating the mutation operations and refinement operations using the modified prompt instruction until reaching a convergence criterion;

retrieving from a vector database a predetermined number of reference examples to be included in the input prompt, by:

encoding the task context data into a vector representation using a sentence transformer model, querying the vector database using the vector representation of the task context data as a query, wherein the vector database stores historical examples of previously performed tasks and associated outcomes, wherein the historical examples are pre-encoded as embedding vectors, wherein the querying of the vector database comprises using a similarity search engine to compute distance metrics between the vector representation of the task context data, and the pre-encoded embedding vectors of the historical examples, identifying the predetermined number of historical examples based on the computed distance metrics, and selecting the predetermined number of identified historical examples for inclusion in the input prompt;

generating the input prompt by combining:

the optimized prompt instruction, the selected predetermined number of identified historical examples, and the task context data for the task; and providing the input prompt to the generative language model to generate a response for performing the task.

2. The method of claim 1, wherein the prompt optimization system operates with configurable parameters comprising:

a number of mutation operations to perform, a number of mutations per operation, a batch size for evaluation samples, and a minimum correct response threshold;

maintains an iterative feedback loop that uses different prompt instruction variations while limiting how many calls are made to generative language models, and continuously improves prompt instruction quality without requiring additional model training; and generates the optimized prompt instruction by:

incorporating knowledge gained from analyzing training examples, adding task intent and expert persona elements, and validating generated content to prevent errors and hallucination.

3. The method of claim 1, wherein the task context data comprises:

a title describing a situation to be analyzed, an initial description of the situation, metadata associated with the situation, and relevant contextual parameters;

wherein the vector database stores historical examples comprising:

previously analyzed situations, verified outcomes of the analyzed situations, contextual parameters associated with the situations, and supporting documentation; and the historical examples are included in the input prompt to provide relevant domain-specific context, enable pattern recognition across similar situations, and guide the generative language model with verified outcomes from analogous cases.

4. The method of claim 1, wherein the task comprises root cause analysis of a computer system incident, and wherein:

the task context data comprises:

an incident title describing an operational incident, an initial incident summary, service identification information, environment parameters, error messages, and system logs;

the vector database stores historical examples comprising:

past operational incidents, verified root causes documented by engineers, configuration changes, performance metrics, system dependencies, and troubleshooting guides;

the generated response comprises:

an identified root cause of the incident, supporting evidence from logs and metrics, relevant historical incident patterns, and recommended mitigation steps.

5. The method of claim 1, wherein the task comprises medical diagnosis, and wherein:

the task context data comprises:

patient symptoms, medical history, test results, vital signs, and relevant contextual health information;

the vector database stores historical examples comprising:
past medical cases,
verified diagnoses,
treatment outcomes,
clinical notes, and
medical reference documentation;
the generated response comprises:
a proposed diagnosis,
supporting clinical evidence,
similar case references, and
recommended treatment options.

6. The method of claim 1, wherein the task comprises code analysis and debugging, and wherein:
the task context data comprises:
error messages,
stack traces,
code snippets,
system configuration, and
execution logs;
the vector database stores historical examples comprising:
past debugging cases,
verified bug fixes,
code patterns,
testing results, and
documentation references;
the generated response comprises:
identified code issues,
supporting analysis,
similar bug patterns, and
recommended fixes.

7. The method of claim 1, wherein the prompt optimization system:
terminates the mutation operations and refinement operations when either:
a predetermined maximum number of iterations has been reached,
no improvement in performance scores is observed over a predetermined number of consecutive iterations, or
a performance score of the best-performing variation exceeds a minimum correct response threshold.

8. A system for generating an input prompt for a generative language model, the system comprising:
at least one processor; and
at least one memory storage device storing instructions thereon, which, when executed by the at least one processor, cause the system to perform operations comprising:
receiving task context data for a task and an initial prompt instruction for instructing the generative language model to perform the task;
generating an optimized prompt instruction with a prompt optimization system that uses one or more generative language models to iteratively apply at least one mutation operation and at least one refinement operation to the initial prompt instruction, wherein:
the at least one mutation operation comprises:
generating multiple variations of the initial prompt instruction via a first call to a first generative language model,
assigning performance-based scores to each variation based on training samples via a second call to a second generative language model, and
selecting a best-performing variation based on the scores;
the at least one refinement operation comprises:

receiving targeted feedback from the second generative language model regarding strengths and weaknesses of the best-performing variation,
modifying the best-performing variation based on the received targeted feedback via a third call to a third generative language model to generate a modified prompt instruction, and
repeating the mutation operations and refinement operations using the modified prompt instruction until reaching a convergence criterion;
retrieving from a vector database a predetermined number of reference examples to be included in the input prompt, by:
encoding the task context data into a vector representation using a sentence transformer model,
querying the vector database using the vector representation of the task context data as a query, wherein the vector database stores historical examples of previously performed tasks and associated outcomes, wherein the historical examples are pre-encoded as embedding vectors, wherein the querying of the vector database comprises using a similarity search engine to compute distance metrics between the vector representation of the task context data, and the pre-encoded embedding vectors of the historical examples,
identifying the predetermined number of historical examples based on the computed distance metrics, and
selecting the predetermined number of identified historical examples for inclusion in the input prompt;
generating the input prompt by combining:
the optimized prompt instruction,
the selected predetermined number of identified historical examples, and
the task context data for the task; and
providing the input prompt to the generative language model to generate a response for performing the task.

9. The system of claim 8, wherein the prompt optimization system operates with configurable parameters comprising:
a number of mutation operations to perform,
a number of mutations per operation,
a batch size for evaluation samples, and
a minimum correct response threshold;
maintains an iterative feedback loop that uses different prompt instruction variations while limiting how many calls are made to generative language models, and continuously improves prompt instruction quality without requiring additional model training; and
generates the optimized prompt instruction by:
incorporating knowledge gained from analyzing training examples,
adding task intent and expert persona elements, and
validating generated content to prevent errors and hallucination.

10. The system of claim 8, wherein the task context data comprises:
a title describing a situation to be analyzed,
an initial description of the situation,
metadata associated with the situation, and
relevant contextual parameters;
wherein the vector database stores historical examples comprising:
previously analyzed situations,
verified outcomes of the analyzed situations,
contextual parameters associated with the situations, and
supporting documentation; and the historical examples are included in the input prompt to provide relevant domain-specific context, enable pattern recognition across similar situations, and guide the generative language model with verified outcomes from analogous cases.

11. The system of claim 8, wherein the task comprises root cause analysis of a computer system incident, and wherein:

the task context data comprises:
an incident title describing an operational incident,
an initial incident summary,
service identification information,
environment parameters,
error messages, and
system logs;
the vector database stores historical examples comprising:
past operational incidents,
verified root causes documented by engineers,
configuration changes,
performance metrics,
system dependencies, and
troubleshooting guides:
the generated response comprises:
an identified root cause of the incident,
supporting evidence from logs and metrics,
relevant historical incident patterns, and
recommended mitigation steps.

12. The system of claim 8, wherein the task comprises medical diagnosis, and wherein:

the task context data comprises:
patient symptoms,
medical history,
test results,
vital signs, and
relevant contextual health information;
the vector database stores historical examples comprising:
past medical cases,
verified diagnoses,
treatment outcomes,
clinical notes, and
medical reference documentation;
the generated response comprises:
a proposed diagnosis,
supporting clinical evidence,
similar case references, and
recommended treatment options.

13. The system of claim 8, wherein the task comprises code analysis and debugging, and wherein:

the task context data comprises:
error messages,
stack traces,
code snippets,
system configuration, and
execution logs;
the vector database stores historical examples comprising:
past debugging cases,
verified bug fixes,
code patterns,
testing results, and
documentation references;
the generated response comprises:
identified code issues,
supporting analysis,
similar bug patterns, and
recommended fixes.

14. The system of claim 8, wherein the prompt optimization system:

terminates the mutation operations and refinement operations when either:
a predetermined maximum number of iterations has been reached,
no improvement in performance scores is observed over a predetermined number of consecutive iterations, or
a performance score of the best-performing variation exceeds a minimum correct response threshold.

15. A computer-readable medium storing instructions thereon, which, when executed by at least one processor, cause a system to perform operations comprising:

receiving task context data for a task and an initial prompt instruction for instructing the generative language model to perform the task:
generating an optimized prompt instruction with a prompt optimization system that uses one or more generative language models to iteratively apply at least one mutation operation and at least one refinement operation to the initial prompt instruction, wherein:
the at least one mutation operation comprises:
generating multiple variations of the initial prompt instruction via a first call to a first generative language model,
assigning performance-based scores to each variation based on training samples via a second call to a second generative language model, and
selecting a best-performing variation based on the scores;
the at least one refinement operation comprises:
receiving targeted feedback from the second generative language model regarding strengths and weaknesses of the best-performing variation,
modifying the best-performing variation based on the received targeted feedback via a third call to a third generative language model to generate a modified prompt instruction, and
repeating the mutation operations and refinement operations using the modified prompt instruction until reaching a convergence criterion;
retrieving from a vector database a predetermined number of reference examples to be included in the input prompt, by:
encoding the task context data into a vector representation using a sentence transformer model,
querying the vector database using the vector representation of the task context data as a query, wherein the vector database stores historical examples of previously performed tasks and associated outcomes, wherein the historical examples are pre-encoded as embedding vectors, wherein the querying of the vector database comprises using a similarity search engine to compute distance metrics between the vector representation of the task context data, and the pre-encoded embedding vectors of the historical examples,
identifying the predetermined number of historical examples based on the computed distance metrics, and
selecting the predetermined number of identified historical examples for inclusion in the input prompt;
generating the input prompt by combining:
the optimized prompt instruction,
the selected predetermined number of identified historical examples, and
the task context data for the task; and
providing the input prompt to the generative language model to generate a response for performing the task.

16. The computer-readable medium of claim 15, wherein the prompt optimization system operates with configurable parameters comprising:

a number of mutation operations to perform,
a number of mutations per operation,
a batch size for evaluation samples, and
a minimum correct response threshold;
maintains an iterative feedback loop that uses different
prompt instruction variations while limiting how many
calls are made to generative language models, and
continuously improves prompt instruction quality with-
out requiring additional model training; and
generates the optimized prompt instruction by:
incorporating knowledge gained from analyzing training
examples,
adding task intent and expert persona elements, and
validating generated content to prevent errors and hallu-
cination.
17. The computer-readable medium of claim 15, wherein
the task context data comprises:
a title describing a situation to be analyzed,
an initial description of the situation,
metadata associated with the situation, and
relevant contextual parameters;
wherein the vector database stores historical examples
comprising:
previously analyzed situations,
verified outcomes of the analyzed situations,
contextual parameters associated with the situations, and
supporting documentation; and
the historical examples are included in the input prompt to
provide relevant domain-specific context, enable pat-
tern recognition across similar situations, and guide the
generative language model with verified outcomes
from analogous cases.
18. The computer-readable medium of claim 15, wherein
the task comprises root cause analysis of a computer system
incident, and wherein:
the task context data comprises:
an incident title describing an operational incident,
an initial incident summary,
service identification information,
environment parameters,
error messages, and
system logs;
the vector database stores historical examples comprising:
past operational incidents,
verified root causes documented by engineers,
configuration changes,
performance metrics, system dependencies, and
troubleshooting guides;
the generated response comprises:
an identified root cause of the incident,
supporting evidence from logs and metrics,
relevant historical incident patterns, and
recommended mitigation steps.
19. The computer-readable medium of claim 15, wherein
the task comprises medical diagnosis, and wherein:
the task context data comprises:
patient symptoms,
medical history,
test results,
vital signs, and
relevant contextual health information;
the vector database stores historical examples comprising:
past medical cases,
verified diagnoses,
treatment outcomes,
clinical notes, and
medical reference documentation;
the generated response comprises:
a proposed diagnosis,
supporting clinical evidence,
similar case references, and
recommended treatment options.
20. The computer-readable medium of claim 15, wherein
the task comprises code analysis and debugging, and
wherein:
the task context data comprises:
error messages,
stack traces,
code snippets,
system configuration, and
execution logs;
the vector database stores historical examples comprising:
past debugging cases,
verified bug fixes,
code patterns,
testing results, and
documentation references;
the generated response comprises:
identified code issues,
supporting analysis,
similar bug patterns, and
recommended fixes.

* * * * *